(12) United States Patent
Znamenskiy

(10) Patent No.: US 10,861,198 B2
(45) Date of Patent: Dec. 8, 2020

(54) METHOD AND APPARATUS FOR SELECTING A MASK USING AUGMENTED FACE SKETCHES

(71) Applicant: KONINKLIJKE PHILIPS N.V., Eindhoven (NL)

(72) Inventor: Dmitry Nikolayevich Znamenskiy, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 64 days.

(21) Appl. No.: 16/023,231

(22) Filed: Jun. 29, 2018

(65) Prior Publication Data

US 2019/0005689 A1 Jan. 3, 2019

Related U.S. Application Data

(60) Provisional application No. 62/527,206, filed on Jun. 30, 2017.

(51) Int. Cl.
*G06T 11/20* (2006.01)
*A61M 16/06* (2006.01)
*G16H 40/40* (2018.01)
*G06T 11/60* (2006.01)

(52) U.S. Cl.
CPC .......... *G06T 11/203* (2013.01); *A61M 16/06* (2013.01); *A61M 16/0605* (2014.02); *G06T 11/60* (2013.01); *G16H 40/40* (2018.01); *A61M 2016/0661* (2013.01); *A61M 2230/00* (2013.01); *G06T 2210/41* (2013.01)

(58) Field of Classification Search
CPC ... G06T 11/203; G06T 11/60; G06T 2210/41; A61M 16/06; A61M 16/0605; G16H 40/40

See application file for complete search history.

(56) References Cited

U.S. PATENT DOCUMENTS

| | | | |
|---|---|---|---|
| 4,453,629 | A | 6/1984 | Goldberg |
| 4,987,615 | A | 1/1991 | Massey |
| 5,584,125 | A | 12/1996 | Prete |
| 6,478,146 | B1 | 11/2002 | Chapman |
| 7,743,920 | B1 | 6/2010 | Lordo |
| 2003/0095701 | A1* | 5/2003 | Shum ................ G06K 9/00221 382/155 |
| 2003/0145859 | A1 | 8/2003 | Bohn et al. |

(Continued)

FOREIGN PATENT DOCUMENTS

| | | |
|---|---|---|
| WO | 2014009914 A2 | 1/2014 |
| WO | WO2016032393 A1 | 3/2016 |

OTHER PUBLICATIONS

Albert Ali Salah, Nese AlyÄuz, Lale Akarun, Registration of 3D Face Scans with Average Face Models, Journal of Electronic Imaging, 17(1), 011006, Jan.-Mar. 2008, oai.cwi.nl/oai/asset/13756/13756B.pdf.

*Primary Examiner* — King Y Poon
*Assistant Examiner* — Vincent Peren
(74) *Attorney, Agent, or Firm* — Michael W. Haas

(57) ABSTRACT

A method of assisting in selection of a particular mask from among a plurality of masks, the method comprising: generating a plurality of augmented faces, each augmented face corresponding to a respective mask of the plurality of masks; and associating each augmented face with a respective mask of the plurality of masks.

12 Claims, 3 Drawing Sheets

(56) References Cited

U.S. PATENT DOCUMENTS

| | | |
|---|---|---|
| 2010/0230314 A1 | 9/2010 | Lordo |
| 2011/0234581 A1 | 9/2011 | Eikelis et al. |
| 2016/0078687 A1* | 3/2016 | Van Bree ............... A61M 16/06 |
| | | 345/419 |

* cited by examiner

METHOD AND APPARATUS FOR SELECTING A MASK USING AUGMENTED FACE SKETCHES

CROSS-REFERENCE TO RELATED APPLICATIONS

This patent application claims the priority benefit under 35 U.S.C. § 119(e) of U.S. Provisional Application No. 62/527,206 filed on Jun. 30, 2017, the contents of which are herein incorporated by reference.

BACKGROUND OF THE INVENTION

1. Field of the Invention

The present invention pertains to methods and apparatuses for use in selecting masks for use in delivering a pressurized flow of treatment gas. More particularly, the present invention pertains to methods and apparatuses for use in such selection which utilize selectively augmented face sketches.

2. Description of the Related Art

The selection of a CPAP mask with proper cushion geometry is one of the key factors determining the mask compliance and therefore the revenue of the mask producer. In this context, the fitting of a CPAP mask to a particular patient is an expensive procedure. First, the masks themselves are expensive, and therefore once fitted they cannot be reused on another person. Second, the fitting of the mask takes time, which is also expensive. Third, the mask fitting can be abusive for the patients. Therefore, actual mask fittings are usually limited to 1-3 masks.

Usually, the durable medical equipment (DME) shop or a sleep lab can have 10-20 different masks, (also including different sizes), from which 1-3 should be selected for an actual fit. This pre-selection is often based on the patient meta-data (e.g., whether the patient is nose or mouth breather, the earlier experience of patient with CPAP masks, etc.), and also the fitting of the patient with CPAP sizing gauges. FIG. 1 shows an example of a flat gauge 10 which is available on the market having a plurality of cushion cut outs 12, 14, 16, 18 which correspond to different cushion sizes. Although such gauge 10 is generally inexpensive, it does not allow for discriminating the fit of more complex sizing schemes which differ in the 3D shape of the mask cushion.

FIG. 2 shows an example of a second type of gauge 20 available on the market which includes a plurality of silicone cushions 22, 24, 26 which correspond to different mask sizes. Such arrangement provides a patient with an impression about the feeling of the actual mask but at the same time such solution has a number of serious limitations. First of all, the cost of gauge 20 is much higher. Also, observe that gauge 20 in FIG. 2 bundles tiny cushions of an alternative mask. The cost of a similar gauge made for a full face mask would be comparable with the cost of the actual mask itself, if not more.

SUMMARY OF THE INVENTION

Accordingly, it is an object of the present invention to provide a method of assisting in selection of a particular mask from among a plurality of masks. The method comprises: generating a plurality of augmented faces, each augmented face corresponding to a respective mask of the plurality of masks; and associating each augmented face with a respective mask of the plurality of masks.

Generating a plurality of augmented faces may comprise generating said plurality of augmented faces using an electronic processing device. Generating a plurality of augmented faces may be carried out by a skilled artist. Generating a plurality of augmented faces may comprise generating a plurality of line sketch augmented faces.

Associating each augmented face with the respective mask of the plurality of masks may comprise displaying each augmented face on packaging associated with, or housing, each respective mask. Associating each augmented face with the respective mask of the plurality of masks may comprise displaying the plurality of augmented faces on a chart along with indicia indicative of the respective mask to which each augmented face corresponds.

Generating each augmented face of the plurality of augmented faces may comprise: determining a group of people who best fit a particular mask of the plurality of masks; and obtaining facial information of the group of people. Obtaining facial information of the group of people may comprise: determining facial dimensions of each member of the group of people; and determining an average face representative of the group from the facial dimensions.

It is another object of the present invention to provide an article associated for use in packaging a mask. The article comprises: a base material; and an augmented face displayed on the base material, wherein the augmented face includes a number of accentuated features indicative of users previously determined to best fit the mask. The augmented face may comprise a line sketch augmented face.

It is yet another object of the present invention to provide a sizing chart for use in selecting a particular mask from a plurality of masks. The sizing chart comprises: a plurality of augmented faces, each augmented face corresponding to a respective mask of the plurality of masks; and indicia associating each augmented face with a respective mask of the plurality of masks. The plurality of augmented faces may comprise a plurality of line sketch augmented faces.

It is yet a further object of the present invention to provide a method of providing a plurality of masks. The method comprises: providing a first mask variant; providing a first augmented face associated with the first mask variant; providing a second mask variant different than the first mask variant; and providing a second augmented face associated with the second mask variant.

Providing a first augmented face associated with the first mask variant may comprise providing the first augmented face on packaging housing, or other material associated with, the first mask variant; and providing a second augmented face associated with the second mask variant may comprise providing the second augmented face on packaging housing, or other material associated with, the second mask variant.

Providing a first augmented face associated with the first mask variant and providing a first augmented face associated with the second mask variant may comprise providing both of the first augmented face and the second augmented face on a single sizing chart.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
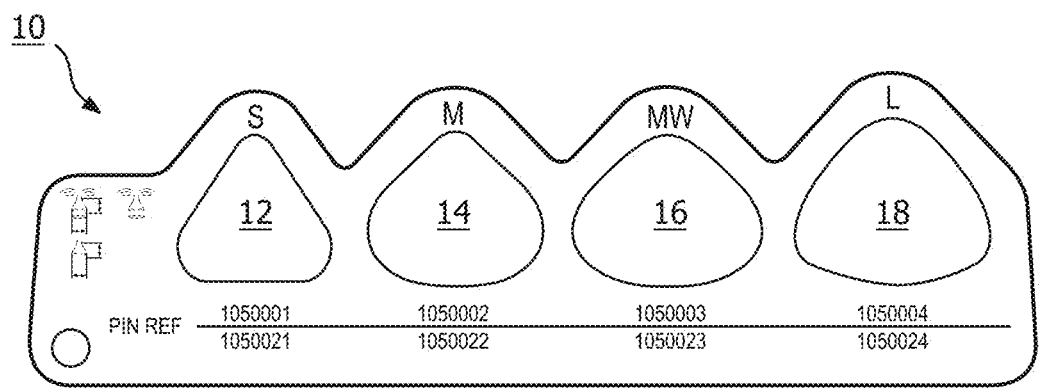
FIG. 1 is an example of a conventional flat sizing gauge for use in determining a size of a mask for a patient.
Figure 2:
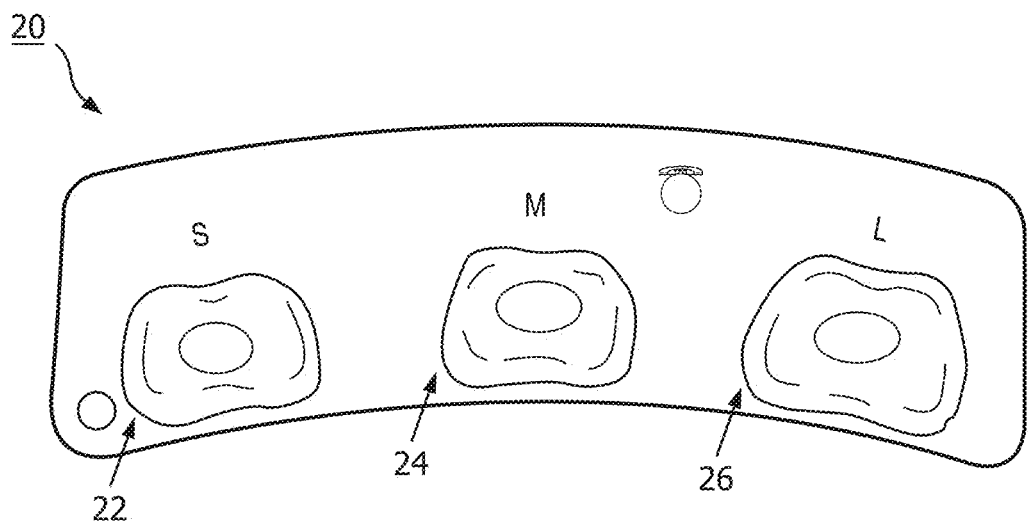
FIG. 2 is an example of another conventional sizing gauge which employs 3-dimensional sizing elements.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the term "augmented face" means a depiction of a human face, whether generated by machine or by human hand, in which one or more features of the face have been exaggerated so as to appear more pronounced or obvious in comparison to other features.

As used herein, the term "features" shall refer to one or more of the cheeks, cheekbones, nose, mouth, brow, upper lip, lower lip, or any other portion of a human face as well as any dimensions thereof or there between such portions. Such term also shall refer to other dimensional characteristics of the human face such as, without limitation, overall width, height, shape, etc.

In creating different mask sizes/variants within a mask family, mask designers commonly: i.) consider facial measurements/characteristics of a given population, ii.) determine a suitable quantity of different masks for adequately fitting such population, and iii.) produce suitable quantities of each mask of the different mask sizes/variants. Embodiments of the present invention provide solutions for identifying the "right" mask from among such different sizes/variants in a given mask family for a particular patient without the need for expensive and/or less than effective sizing gauges. Embodiments of the present invention also provide solutions for confirming that a mask which was originally selected via other means is the correct selection.

Embodiments of the present invention utilize augmented, caricature-like, facial depictions to assist in selecting, and/or confirming a selection of, a suitable mask device for a patient from a plurality of potential mask devices within a mask family (or generally from a group of mask candidates), each having a corresponding augmented facial depiction or "augmented face" associated therewith. Such augmented face generally corresponds to the face of patients to whom the particular device is the best fit from among the plurality of mask devices. Hence, by identifying the augmented face from a family of augmented faces which best matches a patient, the mask device (which corresponds to such augmented face) which most likely best fits the patient is readily determined.

Augmented faces in accordance with embodiments of the present invention may be created in several ways without varying from the scope of the present invention. For best results, the creation of such augmented faces is preferably based on results of previous test fitments of the masks within a group obtained from previous patients. From such previous test fitments, groups of previous users can be identified for which each mask of the group of masks is a best fit. From each group of previous users, an average face which is representative of the group of users which best fit a particular mask, and thus of a representative average face of the group of users which best fits the particular mask can then be determined.

In order to help distinguish each average face from the other average faces, each average face is augmented in a manner which amplifies the differences which are characteristic for a particular average face with respect to the other average faces (and/or which de-emphasizes non-characteristic features).

In one example embodiment of the present invention, such augmentation is carried out by using electronic measurement techniques and computer software programmed to carry out the following steps: 1) for a given population and given mask family, divide the population into sub-groups corresponding to individual mask sizes in the family; 2) compute the average faces corresponding to the individual mask sizes in the family; and 3) for every population participant and every mask compute weight (which can be positive or negative) describing how good of a fit the selected mask size is to the participant against other mask sizes. The weight is positive if the current mask size fits best the participant, otherwise the weight is negative. The weight is higher if the participant is closer to the average face preferring the current mask. In an embodiment the steps 1-3 can be implemented using an automatically registered 3D template face to an extended dataset of 3D facial scans corresponding to a target population. In this registration process an average template face is morphed until it fits every 3D scanned face in the specific set representing the target population group. The use of morphing is well known in the art and commonly referred to as non-rigid registration. An example of such non-rigid registration is described in the Journal of electronic Imaging, Volume 17, Issue 1:011006, January 2008. It is appreciated that such method is provided for exemplary purposes only and that other fully or partially automated techniques may be employed without varying from the scope of the present invention.

Figure 3:
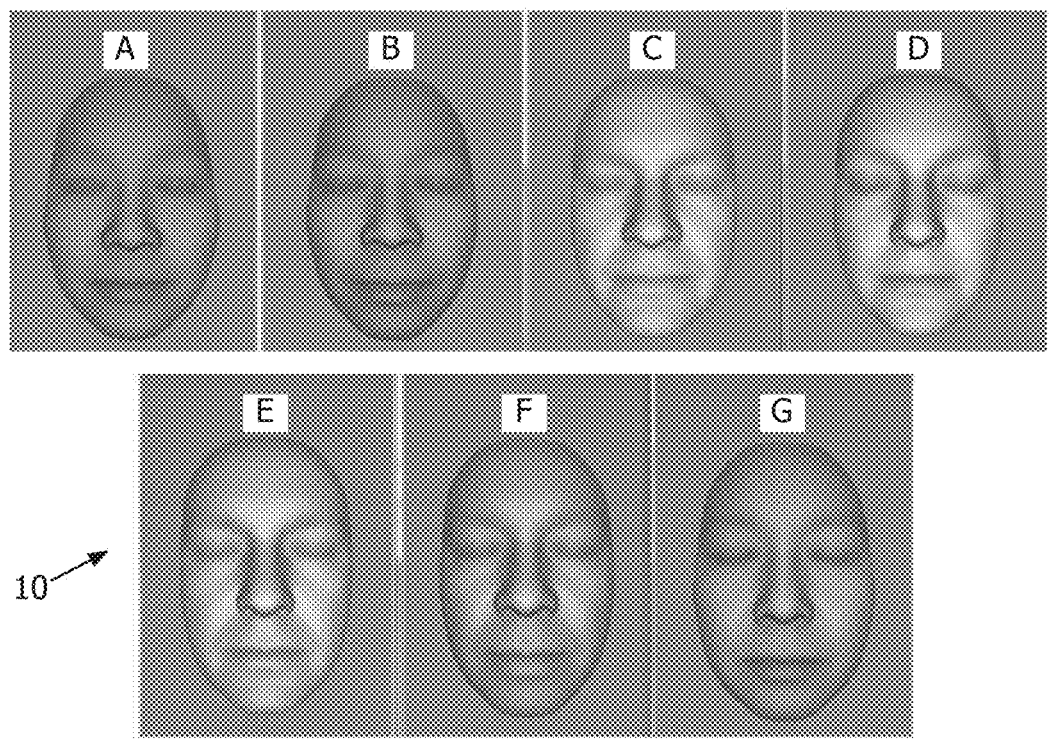
FIG. 3 shows examples of rendered average faces A-G, in accordance with an example embodiment of the present invention, which correspond to seven different size/variants of masks within a particular family of masks.
Figure 4:
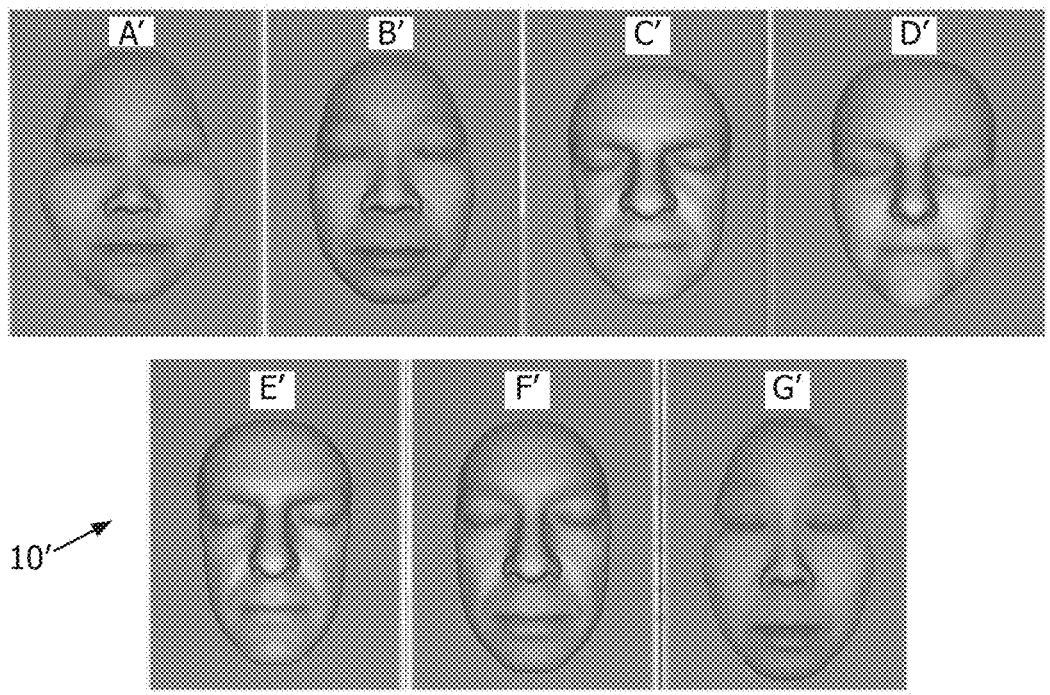
FIG. 4 shows examples of rendered augmented faces A'-G', in accordance with an example embodiment of the present invention, which correspond to the average faces A-G of FIG. 3.

FIG. 3 shows examples of computer renderings of average faces 10, labeled A-G, which correspond to seven different size/variants for a particular family of masks, which were obtained using a generally automated technique. FIG. 4 shows examples of computer rendered augmented faces 10' labeled A'-G' which correspond to average faces A-G of FIG. 3 which were obtained using a generally automated technique such as previously described.

As an alternative, and/or in addition to such computerized/automated methods, it is to be appreciated that creation of augmented faces may also be readily carried out using the perception/artistic skills of a skilled artist (e.g., without limitation, a caricaturist) without varying from the scope of the present invention.

The difference between an average face 10 and an augmented face 10' can be further emphasized by using a (automatic) conversion process to obtain a line sketch augmented face 10" (e.g., in Adobe Photoshop: https://photoshop-tutorials.wonderhowto.com/how-to/convert-photo-into-line-art-drawing-photoshop-160046/). Such conversion can also be carried out by a skillful artist, typically while producing the augmented face (i.e., go directly from average face to line sketch augmented face).

Figure 5:
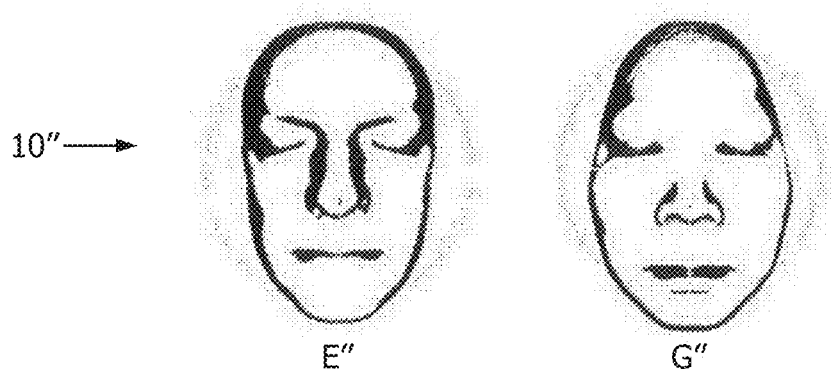
FIG. 5 shows examples of line sketch versions of augmented faces, in accordance with an example embodiment of the present invention, resulting from conversion of two of the augmented faces of FIG. 4.

FIG. 5 shows examples of line sketch augmented faces E" and G" resulting from conversion of augmented faces E' and G' of FIG. 4. The augmented faces 10' of FIG. 4 or the further line sketch augmented faces 10" of FIG. 5 may then be used to assist a patient and/or mask provider in deciding the proper mask for a patient from a family of masks by visually associating the patient's face with one of the augmented faces 10' or line sketch augmented faces 10".

Figure 6:
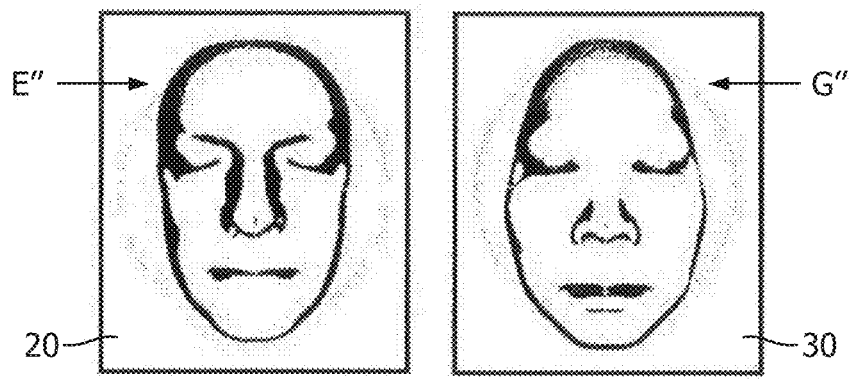
FIG. 6 shows examples of the line sketch versions of FIG. 5 employed on packaging associated with different size/variants within a particular family of masks in accordance with an example embodiment of the present invention.

FIG. 6 shows an example of such use of line sketch augmented faces E" and G". More particularly, FIG. 6 shows an example of a first mask packaging 20 formed of a base material (e.g., without limitation, paper, cardboard), having line sketch augmented face E" displayed thereon, which would be used to house or be otherwise associated with a first mask variant within a mask group. FIG. 6 additionally shows an example of a second mask packaging 30, having line sketch augmented face G" displayed thereon, which would be used to house or be otherwise associated with a second mask variant within the aforementioned mask group. Such packaging 20, 30 can readily be utilized by patients and/or mask providers as a starting point to determine the proper mask for the patient or as a double check after using other methods to verify that the likely correct mask has been selected, by simply evaluating whether the patient's face resembles the line sketch augmented face 10" which is on the mask package (or otherwise associated with the mask).

Figure 7:
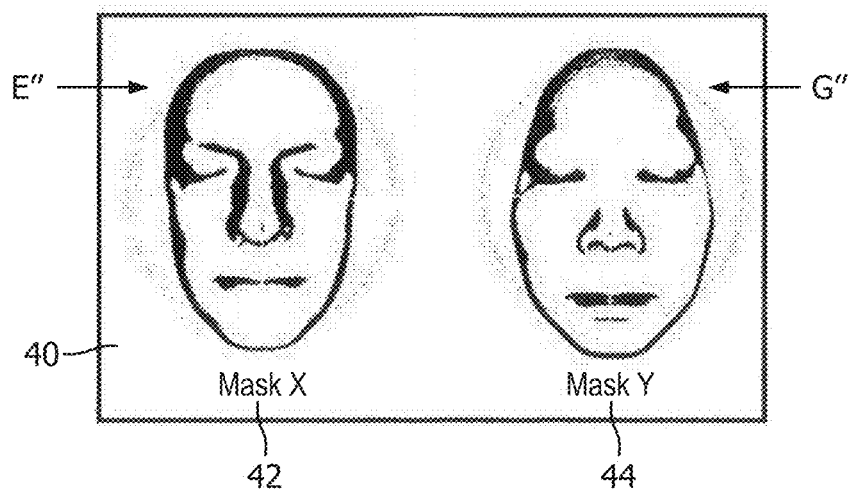
FIG. 7 shows an example of the line sketch versions of FIG. 5 employed on a sizing chart associated with a particular family of masks in accordance with an example embodiment of the present invention.

FIG. 7 shows another example use of the line sketch augmented faces E" and G" of FIG. 5 employed together on a single sizing chart 40 for a particular group of masks. Chart 40 includes indicia 42, 44 associated with each line sketch augmented face E" and G" which indicates the particular mask variants to which each of line sketch faces E" and G" correspond. Such chart 40 can readily be utilized by a patient and/or mask provider to determine the likely best fit mask variant from a particular group/family of masks simply by choosing the line sketch augmented face which most resembles that of the patient. Although described in conjunction with line sketch augmented faces, it is to be appreciated that the example embodiments discussed in regard to FIGS. 6 and 7 can also be carried out using augmented faces such as shown in FIG. 4 which are not in line sketch form. It is also to be appreciated that although shown with only two line sketch augmented faces E" and G", chart 40 may employ other quantities of line sketch faces without varying form the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of assisting in selection of a particular mask from among a plurality of masks, the method comprising:
   generating a plurality of augmented faces, each augmented face corresponding to a respective mask of the plurality of masks; and
   associating each augmented face with the respective mask of the plurality of masks to which each augmented face corresponds, wherein generating each augmented face of the plurality of augmented faces comprises:
   determining a group of people who best fit a particular mask of the plurality of masks; and
   obtaining facial information of the group of people, and wherein obtaining facial information of the group of people comprises:
   determining facial dimensions of each member of the group of people; and
   determining an average face representative of the group from the facial dimensions.

2. The method of claim 1, wherein generating the plurality of augmented faces comprises generating the plurality of augmented faces using an electronic processing device.

3. The method of claim 1, wherein generating the plurality of augmented faces is carried out by a skilled artist.

4. The method of claim 1, wherein associating each augmented face with the respective mask of the plurality of masks comprises displaying the plurality of augmented faces on a chart along with indicia indicative of the respective mask to which each augmented face corresponds.

5. The method of claim 1, wherein generating the plurality of augmented faces comprises generating a plurality of line sketch augmented faces.

6. A method of assisting in selection of a particular mask from among a plurality of masks, the method comprising:
generating a plurality of augmented faces, each augmented face corresponding to a respective mask of the plurality of masks; and
associating each augmented face with the respective mask of the plurality of masks to which each augmented face corresponds,
wherein associating each augmented face with the respective mask of the plurality of masks comprises displaying each augmented face on packaging associated with, or housing, each respective mask.

7. The method of claim 6, wherein generating the plurality of augmented faces comprises generating the plurality of augmented faces using an electronic processing device.

8. The method of claim 6, wherein generating the plurality of augmented faces is carried out by a skilled artist.

9. The method of claim 6, wherein generating the plurality of augmented faces comprises generating a plurality of line sketch augmented faces.

10. A method of providing a plurality of masks, the method comprising:
providing a first mask variant;
providing a first augmented face associated with the first mask variant;
providing a second mask variant different than the first mask variant; and
providing a second augmented face associated with the second mask variant,
wherein the first augmented face was previously created by:
determining a first group of people who best fit the first mask variant; and
obtaining facial information of the first group of people by determining facial dimensions of each member of the first group of people and determining an average face representative of the first group of people from the facial dimensions of each member of the first group of people, and
wherein the second augmented face was previously created by:
determining a second group of people who best fit the second mask variant; and
obtaining facial information of the second group of people by determining facial dimensions of each member of the second group of people and determining an average face representative of the second group of people from the facial dimensions of each member of the second group of people.

11. The method of claim 10, wherein providing a first augmented face associated with the first mask variant comprises providing the first augmented face on packaging housing, or other material associated with, the first mask variant; and wherein providing a second augmented face associated with the second mask variant comprises providing the second augmented face on packaging housing, or other material associated with, the second mask variant.

12. The method of claim 10, wherein providing a first augmented face associated with the first mask variant and providing a first augmented face associated with the second mask variant comprises providing both of the first augmented face and the second augmented face on a single sizing chart.

* * * * *